United States Patent [19]

Sheffner

[11] 4,107,330

[45] Aug. 15, 1978

[54] TOPICAL APPLICATION OF THIOGLYCOLIC ACID IN THE TREATMENT OF ACNE

[76] Inventor: Aaron Leonard Sheffner, 18 Trombley Dr., Livingston, N.J. 07039

[21] Appl. No.: 813,750

[22] Filed: Apr. 4, 1969

[51] Int. Cl.² ............................................. A61K 31/19
[52] U.S. Cl. ..................................... 424/317; 424/347
[58] Field of Search .................................. 424/317, 72

[56] References Cited

PUBLICATIONS

Webber, Handbook of Non-Prescription Drugs, 1967, pp. 104–105.
Harry, Modern Cosmotology, 1962, p. 485.
Sagarin, Cosmetics, Science & Technology, 1957, pp. 468–472.

*Primary Examiner*—Leonard Schenkman
*Attorney, Agent, or Firm*—Cushman, Darby & Cushman

[57] ABSTRACT

A preparation containing as an active ingredient 0.1 to 10% by weight of thioglycolic acid and the salts, esters, and acid amides thereof, is employed in the treatment of acne.

8 Claims, No Drawings

TOPICAL APPLICATION OF THIOGLYCOLIC ACID IN THE TREATMENT OF ACNE

This invention relates to compositions useful in the treatment of acne. More specifically the present invention relates to a pharmaceutical composition containing minor, effective amounts of thioglycolic acid and the salts, esters and acid amides thereof, which composition can be applied topically to soften the skin and render it more permeable, particularly to secretions from the sebaceous glands.

BACKGROUND OF THE INVENTION

The skin covers the surface of the body and consists of two main layers, the epidermis and the subjacent connective tissue layer — the corium, or dermis. The epidermis is a stratified squamous epithelium, the external layer of which keratinizes, or cornifies. The hairs are slender keratinous threads which develop from the matrix cells of the follicular epithelium. Each hair arises in a tubular invagination of the epidermis, the hair follicle, the walls of which are composed of epithelial and connective tissue. One or more sebaceous glands are connected with each hair. Through a short duct they empty their excretion product into the follicular canal in the upper third of its length. In sebaceous glands the secretions result from the destruction of the epithelial cells. These cells break down yielding the oily secretion of the gland, and also a small number of cornified cells.

The epithelial layers are subject to constant mechanical and other trauma. Under certain physiological conditions their cells perish continuously and are shed. This is especially manifest in the epidermis, where the superficial cells are continuously undergoing a peculiar degeneration, called cornification. The cornified cells are constantly desquamated and are replaced by new ones which arise through transformation of the cells of the deeper layers. Part of this transformation involves the oxidation of protein sulfhydryl groups found in keratin (RSH) to disulfides (R—S—S—R). Thus, the surface of the skin contains a large percentage of the protein keratin which is characterized by many disulfide bonds. Under certain circumstances, excessive cornification occurs, and a condition known as hyperkeratinization (hyperkeratosis) develops. (The Cyclopedia of Medicine, Surgery and Specialities, G. M. Piersol, Ed., F. A. Davis Co., Philadelphia, 1946, P. 107.)

The pathological changes common to acne vulgaris consist of a follicular hyperkeratosis and a hypersecretion of sebum. The result of this process is the comedo, or "blackhead," which is composed at its outer end of concentric layers of horny cells, dried sebum, acne bacillus and staphylococci, and at its inner end mainly of sebum. The outer end of the comedo is dark-colored from oxidation of the sebum as well as from dirt. The pressure of the comedo causes some atrophy of the epithelium of the follicle. Sometimes the hyperkeratosis of the mouths of the follicles closes them completely, so that small sebaceous cysts are formed rather than comedones.

Waiting for the spontaneous cure of acne may have tragic results. Early treatment may prevent the number of scars and pits. Many therapeutic procedures have been used. However, the number of new preparations constantly appearing indicates that none of the procedures now used are entirely satisfactory. These methods of treatment include the following: (1) Diet; (2) Keratolytic agents; (3) Antibiotics; (4) Estrogens; (5) Vitamin A; (6) Ultraviolet radiation; (7) Roentgen ray therapy; (8) Surgical removal; and other less frequently used measures. Some of these methods are aimed at decreasing sebaceous gland secretions, others at removing some of the cornified layer of skin or at reducing infection or inflammation. Each of these has undesirable features, however, even though they may produce an amelioration of the acne.

Thioglycolic acid has been used in hair waving lotions and depilatory creams. Other thiol compounds, for example, 2-mercaptopyridine-N-oxide, have been used in shampoos for their antiseptic properties. Topical ointments available for the treatment of diaper rash have been known to contain cysteine. However, the utility of thioglycolic acid and its salts for the treatment of acne and similar dermatological disorders has not been observed previously.

SUMMARY OF THE INVENTION

It has now been observed that the topical application of thioglycolic acid, and the esters, acid amides and salts of thioglycolic acid to the skin of subjects with acne vulgaris and other forms of acne markedly ameliorates the condition. Furthermore, the skin becomes softer, fewer blemishes develop and in general the skin becomes more pleasing in appearance. On continued application of thioglycolate, fewer pimples and comedones appear. Thus, not only is there a therapeutic effect, but also provided is prophylaxis for the condition. Although acne is thought to arise from an overproduction of sebum, and can be controlled in some circumstances by the reduction of sebum formation, there is substantial evidence that acne results primarily because sebum is permitted to accumulate, due in large measure to stoppage of the sebaceous gland ducts or the follicular ducts as excessive keratinization (cornification) occurs. It is reasonable to expect that if the ducts remain patent, even relatively large amounts of sebum will be permitted to escape on to the surface of the skin. Under such circumstances, the skin might become oily, however, pimples, comodones, and fatty cysts will not develop.

Thioglycolic acid is known to break disulfide bonds such as occur in keratin (Cecil, R., and J. R. McPhee, 1959, Adv. in Prot. Chem., Vol. 14:255). Thus application of thioglycolic acid to the surface of skin increases the permeability of the skin and maintains the patency of ducts leading on to the skin.

Thioglycolic acid and its derivatives described herein, though toxic in concentrated form, are relatively non-toxic when applied topically in the appropriate dilutions. Thioglycolic acid is considerably less irritating and sensitizing, for example, than is generally the case for other sulfhydryl compounds. For this reason salts of thioglycolic acid have been used for many years without difficulty in hairwaving lotions. When applied to the skin of subjects with acne there is a favorable response within 2 to 3 days. Continued use reduces further formation of pimples, comedones and blemishes. The compounds may be applied in a wide variety of pharmaceutical forms such as a solution, lotion, ointment, jelly, cream, powder, shampoo, aerosol, lipstick, shaving preparation, perfume or cologne. The preparation should remain in contact with the skin at least several hours each day. The concentrations used may vary from 0.1% to 10%. Above 10% irritation to the skin may occur on continued usage. Preferred concentrations are 1% to 5% and most preferred 1–2%. The choice of concentration will depend on the nature of the preparation and the anticipated period for which it will remain in contact with the skin.

DESCRIPTION OF THE PREFERRED EMBODIMENTS

The preferred compound with which the present invention is concerned is thioglycolic acid. In addition to the acid itself, the present invention concerns use of their non-toxic salts, either metals or nitrogenous bases. The esters and carboxamides of thioglycolic acid are also included. The nitrogenous portion of the carboxamides of thioglycolic acid may be an amino group having one or two hydrogen atoms or not more than two N-substituents selected from alkyl, alkenyl, cycloalkyl or cycloalkenyl, each having not more than 6 carbon atoms and substituted by not more than two groups selected from hydroxyl, mercepto or carboxyl; or it may be a heterocyclic group such as piperazino, pyrrolidino, piperidino, or morpholino. The operable esters of thioglycolic acid are the lower alkyl and lower alkenyl esters, each having not more than 6 carbon atoms in the ester group.

The preferred compounds of the present invention may be described as follows:

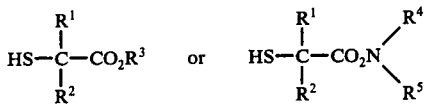

In these formulas $R^1$, $R^2$, $R^3$, $R^4$ and $R^5$ may be hydrogen atoms, lower alkyl groups of not more than 6 carbon atoms, or lower alkenyl groups of not more than 6 carbon atoms. $R^4$ and $R^5$ may be joined to form a heterocyclic structure which includes the nitrogen atoms to which they are usually attached.

When used in solution the following thioglycolates are preferred: metal salts including sodium, potassium, ammonium, calcium, magnesium, and aluminum; nitrogenous salt-forming bases are ammonia, ethanolamine, triethanolamine, triethylamine, piperazine.

Representative compounds useful in this invention include thioglycolic acid, thioglycolic amide, and thioglycolic ethyl ester. The acids referred to above may be neutralized when formulated into topical preparations. Adjustment of pH is accomplished by suitable alkaline reacting substances such as sodium hydroxide, ammonium hydroxide or organic bases. The salts may also be prepared as dry solids for use in dry preparations such as dusting powders or aerosols.

Processes for preparing the active ingredients employed in this invention are known to those skilled in the art. Thioglycolic acid, for example, can be prepared by the action of sodium sulfhydrate on sodium chloroacetate (p. 1037 Merck Index 1960).

The preferred compound for use in the present invention is thioglycolic acid and its pharmaceutically and cosmetically acceptable salts. The safety of these compounds is established through long use of the ammonia and sodium salts in cold hairwaving and the calcium salt as a depilatory.

As previously pointed out, undiluted thioglycolic acid is highly toxic and is a severe eye and skin irritant; however, the primary irritation decreases considerably with dilution, and at 2-10% there is no significant irritation. Further, thioglycolic acid was not a potent sensitizer in guinea pigs. Skin irritation has occasionally occurred in professional hairdressers, but is relatively rare in home use where lower concentrations are used. Specific sensitization is rare, thus favorably distinguishing this substance from most other sulfhydryl compounds. The sulfhydryl moiety of thioglycolic acid reacts rapidly with the disulfide bonds of keratin, more so, for example, than cysteine and its derivatives. Consequently, thioglycolic acid can be used in much lower concentrations, i.e., in the range of 1-2%, for the purpose of treating acne. Also, protein molecules are penetrated more rapidly and deeply by thioglycolic acid than by cysteine and its derivatives, thus permitting more intensive therapy. From a commercial aspect, thioglycolic acid is considerably less expensive to manufacture and is used at considerably lower concentrations than are other sulfhydryl compounds sufficiently innocuous for use with humans.

Directions for preparing several compositions useful in practicing the present invention are presented below.

COMPOSITIONS 1. 5% Thioglycolic Acid Solution

Thioglycolic acid: 5.0 g.
Hexachlorohene: 1.0 g.
Disodium EDTA: 0.05 g.
Sodium hydroxide qs: pH 7.0
Distilled water: 100 ml.

Disodium EDTA is a metal salt complexing agent which reduces the oxidation of the sulfhydryl group of thioglycolic acid by removing trace metal from solution. These trace metals catalyze the oxidation of sulfhydryl groups. Sodium hydroxide is added only to bring the solution to pH 7.0. Although most acne preparations are at pH 5.0, the thioglycolic acid is less effective at acid pH levels. Alternatively the sodium salt of thioglycolic acid may be used.

The solution should be prepared bacteria and mold-free by filtration through a bacteriological filter. For additional preservative action 80 mg. methylparaben and 20 mg. propylparaben may by added.

2. 1% Thioglycolic Acid Jelly

A composition made with a clear, washable jelly containing 1% thioglycolic acid as the sodium salt and having the following ingredients:

Thioglycolic acid: 1.0 g.
Carboxyvinyl polymer: 2.5 g.
Sodium hydroxide: to pH 7.0
Hexachlorophene: 1.0 g.
Disodium EDTA: 0.05 g.
Glycerin: 5.0 g.
Distilled water qs: 100 g.

3. 2% Thioglycolic Acid Lotion

A lotion comprising the following materials, plus fragrances and substances to mask the odor of thioglycolic acid, is prepared as follows:

Thioglycolic acid: 2.0 g.
Triethanolamine: to pH 7.0
Disodium EDTA: 0.05 g.
Calamine: 8.0 g.
Hexachlorophene: 1.0 g.
Distilled water qs: 100 ml.

4. Powder Containing 2% Thioglycolate

A powder containing sodium thioglycolate is prepared to contain the following items:

Micronized sodium thioglycolate: 2 g.
Talc U.S.P. 97 g.
Hexachlorophene: 1 g.

Perfumes are added as needed to mask the odor of sodium thioglycolate.

5. Ointment Containing 1% Thioglycolic Acid

An ointment containing thioglycolic acid is prepared to contain the following materials:

Sodium thioglycolate: 1.2 g.
Disodium EDTA: 0.5 g.
Methylparaben: 0.25 g.
Propylparaben: 0.15 g.
Sodium lauryl sulfate: 10.0 g.
Tetracycline hydrochloride: 0.5 g.
Propylene glycol: 120.0 g.
Stearyl alcohol: 250.0 g.
Sodium hydroxide qs: pH 5.0
White petrolatum: 250.0 g.
Distilled water qs: 1000 ml.

Melt the stearyl alcohol and the white petrolatum on a steam bath and warm to about 75° C. Add the other ingredients, previously dissolved in water and warmed to 75° C; adjust the pH to 5.0 and stir the mixture until it congeals.

EXAMPLE 1

Effect of Topical Application of 10% Sodium Thioglycolate Solution on the Complexion of Teen-Age Children with Acne Two teen-age children — a male aged 16 and a female aged 14 — with a moderate degree of acne were the subjects of this experiment. A solution containing 10% sodium thioglycolate in 0.9 sodium chloride (pyrogen-free for injection), pH 7.0, was applied to one half of the face, either the right or left side, of each subject each night before retiring. Prior to application of the thioglycolate solution, the face of each subject was washed with a detergent bar and thoroughly rinsed. The thioglycolate solution was applied by saturating sterile cotton and wiping the face with the wet cotton. Only one half of the face was so treated, the remaining side serving as a control. The side of the face chosen for treatment was the one considered to have a more severe form of acne.

After three days of treatment for both subjects, the side of the face receiving thioglycolate contained fewer pimples and comedones, and was remarkably smoother, containing fewer blemishes and scabs. This condition was maintained until the experiment was terminated after 7 days' treatment. With the male subject, the treated side was somewhat reddened, but no other sign of irritation was observable.

EXAMPLE 2

Effect of 5% Sodium Thioglycolate Solution on the Complexion of Children with Acne The experiment of Example 1 was performed except with 5% thioglycolate. It was observed that within 12 hours the treated side of the face was smoother, softer and had fewer blemishes.

EXAMPLE 3

Effect of 5% Sodium Thioglycolate Solution on the Complexion of an Adult Woman

A 5% sodium thioglycolate solution (in 0.9% sodium chloride, pH 7.0) was applied with a cotton pledget to one side of the forehead of a 42 year old woman. The forehead was moderately wrinkled and contained a few blemishes. After the solution was applied twice a day for 3 days, the treated side of the forehead was appreciably softer and had fewer blemishes.

A small fatty cyst on the side of the face was treated separately in a similar fashion, and this cyst became much smaller and softer after 3 applications over a period of 24 hours.

What is claimed is:

1. A process for treating acne comprising:
    (1) applying to the acne affected skin of a person suffering therefrom, an acne alleviating amount of a topical composition containing 0.1% to 10% by weight of thioglycolic acid or a pharmaceutically acceptable salt thereof, and
    (2) keeping said composition in contact with the affected skin for several hours.
2. The process of claim 1 wherein said thioglycolic acid is applied topically in the form of a pharmaceutically acceptable acid solution of the following composition:
    Thioglycolic acid: 5.0 g.
    Hexachlorophene: 1.0 g.
    Disodium EDTA: 0.05 g.
    Sodium hydroxide qs: pH 7.0
    Distilled water: 100 ml.
3. The process of claim 1 wherein said thioglycolic acid is applied topically in the form of a pharmaceutically acceptable lotion of the following composition:
    Thioglycolic acid: 2.0 g.
    Triethanolamine: to pH 7.0
    Disodium EDTA: 0.05 g.
    Calamine: 8.0 g.
    Hexachlorophene: 1.0 g.
    Distilled water qs: 100 ml.
4. The process of claim 1 wherein said thioglycolic acid is applied topically in the form of a pharmaceutically acceptable ointment of the following composition:
    Sodium thioglycolate: 1.2 g.
    Disodium EDTA: 0.5 g.
    Methylparaben: 0.25 g.
    Propylparaben: 0.15 g.
    Sodium lauryl sulfate: 10.0 g.
    Tetracycline hydrochloride: 0.5 g.
    Propylene glycol: 120.0 g.
    Stearyl alcohol: 250.0 g.
    Sodium hydroxide qs: ph 5.0
    White petrolatum: 250.0 g.
    Distilled water qs: 1000 ml.
5. The process of claim 1 wherein said concentration is 0.1% to 5% by weight.
6. The process of claim 5 wherein said concentration is 0.1 to 2% by weight.
7. The process of claim 1 wherein 0.1 to 5% by weight of the sodium salt of thioglycolic acid is applied topically to the skin.
8. The process of claim 7 wherein 0.1 to 2.0% by weight of the sodium salt of thioglycolic acid is applied topically to the skin.

* * * * *